(12) United States Patent
Dupont et al.

(10) Patent No.: US 6,960,867 B2
(45) Date of Patent: Nov. 1, 2005

(54) INSTALLATION WITH PIEZOELECTRIC ELEMENT FOR EQUIPPING A STRUCTURE AND PIEZOELECTRIC ELEMENT FOR SAME

(75) Inventors: Marc Dupont, Bures sur Yvette (FR); Marc Pernice, Fresnes (FR); Elisabeth Roy, Massy (FR)

(73) Assignee: ONERA (Office National d'Etudes et de Recherches Aerospatiales), Chatillon (FR)

( * ) Notice: Subject to any disclaimer, the term of this patent is extended or adjusted under 35 U.S.C. 154(b) by 89 days.

(21) Appl. No.: 10/221,938

(22) PCT Filed: Mar. 22, 2001

(86) PCT No.: PCT/FR01/00867

§ 371 (c)(1),
(2), (4) Date: Dec. 2, 2002

(87) PCT Pub. No.: WO01/71953

PCT Pub. Date: Sep. 27, 2001

(65) Prior Publication Data

US 2004/0046483 A1    Mar. 11, 2004

(30) Foreign Application Priority Data

Mar. 23, 2000 (FR) .................................. 00 03721

(51) Int. Cl.[7] ............................................. H01L 41/08
(52) U.S. Cl. ...................... 310/322; 310/317; 310/319; 310/328; 310/334
(58) Field of Search ........................ 310/313 A, 313 B, 310/313 C, 313 D, 321, 322, 334, 328, 317, 310/319

(56) References Cited

U.S. PATENT DOCUMENTS

| 3,771,772 A | * | 11/1973 | Honda ........................ 366/110 |
| 3,855,847 A | * | 12/1974 | Leschek ...................... 73/587 |
| 4,380,931 A | | 4/1983 | Frost et al. |
| 4,779,452 A | | 10/1988 | Cohen-Tenoudji et al. |
| 5,298,828 A | * | 3/1994 | Radovanovich ............. 310/319 |
| 6,744,367 B1 | * | 6/2004 | Forster .................... 340/572.7 |

FOREIGN PATENT DOCUMENTS

WO    WO 9522065    8/1995

* cited by examiner

Primary Examiner—Mark Budd
(74) Attorney, Agent, or Firm—Stites & Harbison PLLC; Douglas E. Jackson

(57) ABSTRACT

The invention concerns an installation with piezoelectric element for transmitting or receiving ultrasonic waves in a structure, the electrodes (8) of said element (7) being connected, as the case may be, to a powering circuit producing energizing electric signals designed to enable it to transmit ultrasonic signals in said structure (6), or to a circuit receiving electric signals transmitted by said element under an energizing ultrasound received by it from said structure, said piezoelectric element (7) being integrated in the structure. The powering or receiving circuits of said piezoelectric elements (7) consist each of a magnetic induction loop (9) likewise comprised in the structure (6) and capable of receiving from an external circuit (10, 11) or respectively transmitting thereto, electromagnetic signals.

17 Claims, 2 Drawing Sheets

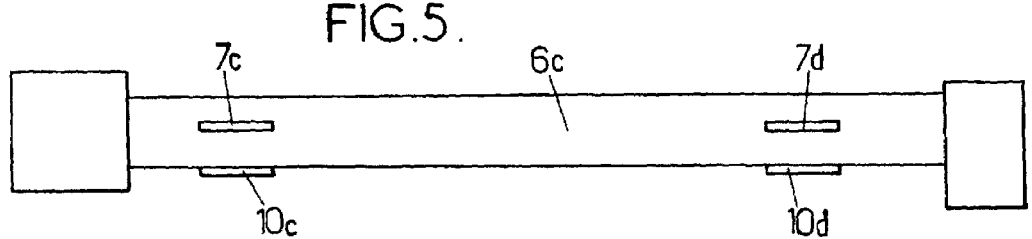
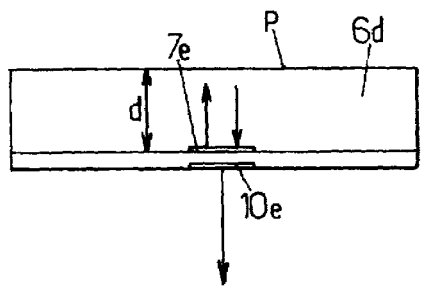
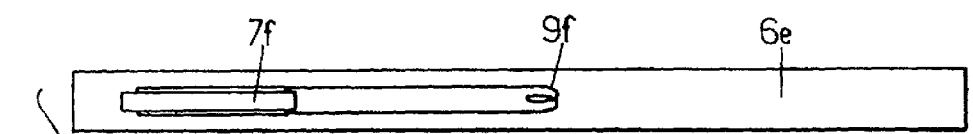

INSTALLATION WITH PIEZOELECTRIC ELEMENT FOR EQUIPPING A STRUCTURE AND PIEZOELECTRIC ELEMENT FOR SAME

The present invention concerns, first of all, an installation with a piezoelectric element for transmitting or receiving ultrasonic waves in a structure, for example a structure to be inspected, the electrodes of this element being connected, depending on the circumstances, to a power supply circuit producing electrical excitation signals capable of inducing it to transmit ultrasonic signals in said structure, or to a circuit for receiving electrical signals transmitted by said element as a result of an ultrasonic excitation it receives from said structure, said piezoelectric element being incorporated into the structure.

The invention also concerns a piezoelectric element specially designed to be used in such an installation.

The structures more particularly involved in the invention are, without indicating any limiting characteristics, composite structures composed of impregnated durable fibers, for example of the carbon epoxy or glass resin type, used primarily in the construction of transport vehicles of all types (air, automotive, marine, rail) because of the fact that they have good mechanical properties, fatigue strength and corrosion resistance, under a relatively low load. In order to meet the safety requirements imposed, particularly in this technical field, it is necessary to examine these structures regularly during systematic, and sometimes even continuous, inspections. Thus, there is a tendency to develop installations comprising a structure to be inspected and the sensor or sensors of its own inspection system, which are integrated, i.e., permanently incorporated, into the structure during the production of the latter. This technique facilitates the inspection of the structures involved, which are equipped, by design, with the sensors required for this inspection.

This being the case, it is understood that in such installations the elements incorporated into the structures in question must not diminish the mechanical properties of these structures, and must therefore be of very small dimensions. That is the reason why the most appropriate elements at the present time are certainly piezoelectric elements, of a ceramic or similar type, which can be produced in very small sizes and which make it possible to continuously or regularly perform an ultrasonic scan of the material of the structure, the internal defects of the latter being translated into modifications of the characteristics of the transmission of the pressure field in this structure, for example between a piezoelectric element serving as an ultrasound transmitter and another piezoelectric element serving as a sensor of the ultrasonic waves transmitted by the transmitter; the same piezoelectric element can also serve, in certain cases, either simultaneously or alternately, as a transmitter and a receiver.

The integration of such piezoelectric elements of small dimensions into structures of the type described above does not pose any particular problem, whether these structures are produced by stacking pre-impregnated, heat- and pressure-polymerized layers, or whether they are produced by compression and injection molding a resin incorporating the durable fibers.

A problem does arise, however, at the level of the connections, especially in complex structures comprising several parts P1, P2, etc., manufactured separately and then assembled, as represented schematically in FIG. 1 of the attached drawing. In essence, it is appropriate in this case to provide connectors at the interfaces between parts and at at least one end of the structure, for the input and/or the output of an electrical signal. FIG. 1 represents by way of example an installation comprising a piezoelectric element 1 integrated into the part P1 and connected to an input and/or output connector 2 by wires 3, 4 and an interface connector 5 connecting the two wires. Thus, there is a direct link with the power supply and/or data acquisition device, and this technique is directly applicable to prototype studies in the laboratory, but with the following major drawbacks: links by means of wires and connectors make the production of each piece of the structure complex and costly, making this production not very suitable for long runs, and machining the piece (for example cutting the edges) after the integration of the piezoelectric element is impossible.

The object of the present invention is to eliminate these drawbacks of the prior art by eliminating any link between piezoelectric elements by means of electrical wires inside the structure, or even outside the latter, and the power supply and/or testing and measuring devices.

To this end, an installation according to the present invention of the type mentioned at the start is characterized in that the power supply or receiving circuits of the piezoelectric element are each constituted by a magnetic induction loop, also incorporated into the structure and capable of receiving from an external circuit, or respectively of transmitting to it, electromagnetic signals.

Advantageously, the magnetic induction loop is constituted by a flat spiral of a flexible printed circuit, a positioning mark located on the surface of said structure being provided next to said spiral.

In a variant, the magnetic induction loop is constituted by a flat spiral of a printed circuit etched directly onto the piezoelectric element; it thus fulfills the additional function of an electrode of this element.

This way, the assembly of the piezoelectric wafer and the magnetic induction loop can remain extremely flat, cannot constitute an extra thickness on the surface of the structure, and does not substantially modify the geometric and mechanical properties of the latter.

A piezoelectric element and a magnetic induction loop having reversible operations, it is understood that the invention could fall into two different categories of concepts, depending on whether the piezoelectric element is used as an ultrasound transmitter or as an ultrasound sensor.

Thus, an installation according to the invention can also be characterized either in that said external circuit is constituted in the form of a primary winding of a transformer connected to an alternating current supply source and induction-coupled to said magnetic induction loop constituting the secondary of said transformer, said piezoelectric element in this case constituting a transmission source for ultrasonic waves in said structure, or in that this external circuit is conversely constituted in the form of a secondary winding of a transformer connected to a circuit for processing the signal and induction-coupled to said magnetic induction loop constituting the primary of said transformer, said piezoelectric element in this case constituting a receiver of ultrasonic waves transmitted in said structure.

In the latter case, it is possible to perform a monitoring of the acoustic transmissions of potential damage to the structure, in an intrinsically known way. The piezoelectric elements in this case act as receivers, in frequency ranges that can be between 100 kHz and 1 MHz.

The installation could also be characterized in that it simultaneously comprises both types of piezoelectric elements arranged in pairs, one of which constitutes a transmitter or receiver of ultrasonic waves, the other conversely a receiver or transmitter, since each, as indicated above, is reversible.

An installation according to the invention could therefore also be characterized in that it comprises at least one first and one or more second piezoelectric elements incorporated into the structure, the first element being associated with a magnetic induction loop constituting the secondary of a first transformer induction-coupled to the primary winding constituted by an external circuit connected to an alternating current supply source, said first piezoelectric element in this case constituting a transmission source for ultrasonic waves in said structure, and the second element or elements each being associated with a magnetic induction loop constituting the primary of a second transformer induction-coupled to the secondary winding constituted by an external circuit connected to a circuit for processing the signal, the second piezoelectric element or elements in this case constituting one or more receivers of the ultrasonic waves transmitted in this structure by the first piezoelectric element.

According to a yet another variant of the invention, it is also possible to use one and the same piezoelectric element as an ultrasonic wave transmitter and as a receiver, in order to measure for example the travel time of impulse waves transmitted by this element in the structure, from their reflection on a surface (or an internal defect), and their return to the element. This way, it is possible to continuously measure the erosion rate of a surface, for example of the surface of a heat shield in the process of ablating.

In all cases, it would of course also be advantageous to produce said two windings in the form of flat spirals, capable of being attached to said structure next to said magnetic induction loops, so as to obtain flat transformers, with an excellent magnetic coupling.

Also advantageously, it is possible to provide for a film of magnetic material to be intercalated between each external transformer winding and the corresponding magnetic induction loop, incorporated into said structure in order to further strengthen this magnetic coupling.

However, the transmission of signals to the magnetic induction loop of a piezoelectric element integrated into a structure can be performed remotely, without a transformer, especially when the signals are required by the nature of the inspection to be transmitted at high frequency, for example in the 50 kHz to 1 MHz band, in order to perform the non-destructive inspection of a structure by shearography. In this case, an installation according to the invention of the type mentioned at the start is characterized in that the structure, equipped with at least one piezoelectric element that is incorporated into it with its magnetic induction loop, is associated with a transmission source for electromagnetic signals in the frequency range required by the non-destructive inspection envisaged, and in case of inspection by shearography, with an optical system for displaying the ultrasonic waves transmitted in the structure, said source and said system being located at a distance from said structure.

The invention also concerns the piezoelectric elements themselves, as well as the shape characteristics of the magnetic induction loops that are associated with them. These characteristics, as well as certain dimensional indications, will be given below, in connection with the following description of certain non-limiting exemplary embodiments, given with reference to the other figures in the drawing, in which:

FIG. 5 represents the schematic configuration of a structure equipped with both ultrasound transmitting piezoelectric elements and receiving piezoelectric elements;

FIG. 6 represents the use of the invention for measuring the ablation rate of the surface of a structure; and FIG. 7 is a diagram of an installation for transmitting electromagnetic waves in a structure equipped according to the invention, this installation allowing a remote and non-destructive inspection of this structure by shearography.

Figure 1:
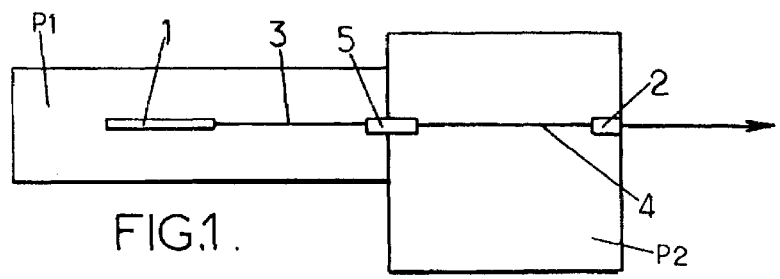
Figure 2:
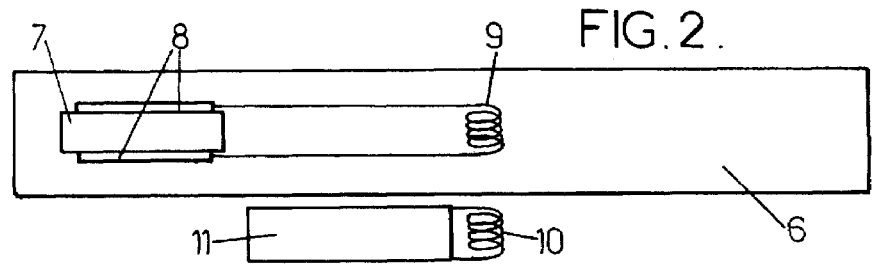
FIG. 2 represents the schematic diagram of a magnetic coupling link between an external winding and a piezoelectric element incorporated into a structure made of composite material.

In FIG. 2, the composite structure is referenced 6 and incorporates by design, according to any of the methods indicated above, a thin piezoelectric element 7 whose electrodes 8 are connected to the ends of a magnetic induction loop 9, also incorporated into the structure and advantageously formed into a flat spiral. This loop is coupled by magnetic induction to the flat winding 10 of a transformer connected to an electronic circuit 11, this winding being attached in temporary or permanent fashion to the structure 6 next to the loop 9. The circuit 11 can be constituted by an alternating current supply source, in which case the winding 10 is considered to be the primary of a transformer whose secondary is constituted by said loop 9, the piezoelectric element 7 in this case being a device for transmitting ultrasounds in the structure 6. It can also be a circuit for amplifying received signals, in which case the winding 10 is considered to be the secondary of a transformer whose primary is constituted by the loop 9, the piezoelectric element in this case being a device for receiving ultrasounds transmitted in this structure 6.

Thus, one obtains a miniature element that can be easily integrated into any durable structure and that makes it possible to transmit to an external circuit, or to receive from it, any signal usable for the continuous or systematic inspection of this structure. For example, the magnetic induction loop can be made of a thin, flexible printed circuit type layer, with a thickness of 50 to 100 m, and the piezoelectric element, which can be disposed at the center of the spiral of the loop 9, can be in the form of a wafer with a thickness on the order of 100 m. For example, a prototype integrated into two plates of carbon-epoxy composite material with a thickness of 4 mm was produced. The piezoelectric element 7 had a diameter of 5 mm and a thickness of 100 m. The spiral loop 9 comprised two superposed spirals of 18 turns each, with an external diameter of 25 mm and an internal diameter of 10 mm, supported by two Kapton films.

As for the calculation of the transformer, possibly using magnetic materials, it merely makes use of current knowledge on the subject, and does not need to be detailed here. It should be noted, however, that it would be advantageous to also provide windings 10 or the like in the form of flat double spirals, wound so that their fluxes are combined, and at a very short distance from one another (on the order of 0.1 mm); each spiral can comprise, for example, 17 turns and have a thickness of 18 m.

The magnetic coupling in the transformers thus constituted is a function of the distance between the loops and the windings for a given geometry, and it may be assumed that the losses of flux measured are negligible for a distance of less than 2 mm; beyond that, attenuation is observed. As for the magnetic transparency of the materials, it should be noted that it is a function of their electrical conductivity and their thickness. All dielectrics have good magnetic transparency in a frequency range of up to 10 MHz.

Figure 3:
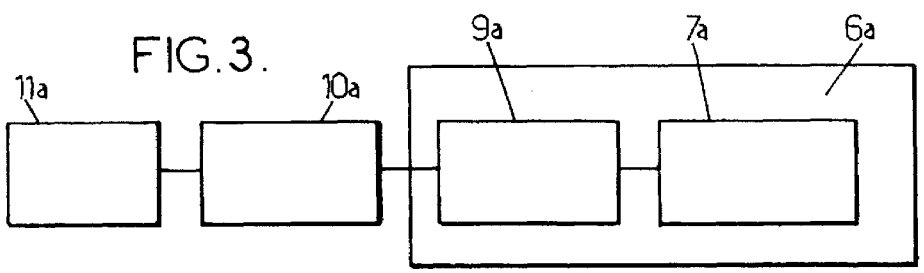
FIG. 3 represents the schematic configuration for generating ultrasounds in a structure.

FIG. 3 represents another installation according to the invention, comprising a composite structure 6a integrating a piezoelectric element 7a designed to generate ultrasounds in the structure, and wherein the magnetic induction loop 9a is established as the secondary of a transformer whose primary winding 10a, attached to the loop, is connected to a variable frequency current supply source 11a.

Figure 4:
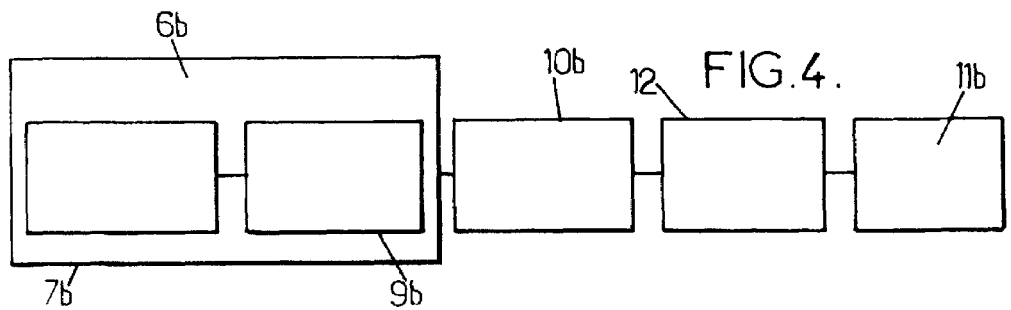
FIG. 4 represents the schematic configuration for detecting ultrasounds transmitted in a structure.

With an analogous technology, FIG. 4 represents another installation according to the invention, comprising a composite structure 6b integrating a piezoelectric element 7b designed to constitute a receiver of ultrasounds transmitted in the structure, and wherein the magnetic induction loop 9b, connected to the electrodes of the element, is established as the primary of a transformer whose secondary winding 10b, attached to the loop, is connected to a signal processing circuit 11b by means of an amplifier and filter assembly 12.

FIG. 5 represents an installation comprising a structure made of composite material 6c into which are integrated two piezoelectric elements 7c and 7d, both of which can function as an ultrasound transmitter or receiver (the drawing being simplified, the magnetic induction loops associated with these elements are not represented). The corresponding windings of the transformers are represented here, also in schematic fashion, by 10c and 10d. These transformers can be used for transmitting or receiving electrical signals, depending on whether the associated piezoelectric element 7c or 7d is intended to transmit or receive ultrasounds.

FIG. 6 represents an installation used in a structure 6d whose thickness can vary, for example being reduced by ablation or wear, or increased, for example by ice accretion. This structure is equipped with a piezoelectric element that is both an ultrasound transmitter and receiver 7e coupled by magnetic induction to an external circuit winding 10e connected to a measuring and impulse current supply system, at a frequency of several hundred kHz. The ultrasound impulses transmitted by the element 7e to the wall P subject to a variation in thickness are reflected off this wall and received by the element 7e with a delay time that will thus provide, advantageously continuously, a measurement of the variation in the thickness of the structure.

Lastly, FIG. 7 represents another installation according to the invention, in which the structure 6e, equipped with at least one piezoelectric element 7f that is incorporated into it with its magnetic induction loop 9f, is associated with a source 10f, 11f for transmitting electromagnetic signals in the frequency range required by the non-destructive inspection envisaged, and in case of an inspection by shearography, with an optical system 12 for displaying the ultrasonic waves transmitted in the structure by the element 7f, said source 10f, 11f and said system 12 being located at a distance from said structure 6e. This inspection principle can be applied to all cases in which it is necessary to have high-frequency mechanical stress, as in the case of shearography. Of course, the power of the transmission source 10f, 11f must be sufficient to excite the piezoelectric element 7f by means of the magnetic flux generated remotely in its loop 9f, so that it transmits ultrasounds in the structure; the remote display, by the system 12, of the ultrasonic waves in the structure 6e, provides information on its potential damage.

In the preceding examples, it was assumed that the structure was a structure to be inspected, but the invention is not always limited to this application. It could be any structure, for example a structure serving merely as a transitional medium for the transmission of data between two other structures or devices.

It is also important to note that any combination of piezoelectric elements in the structure is possible, for example several piezoelectric receivers for receiving the signals from a single transmitting element, or vice versa, as mentioned above.

What is claimed is:

1. Installation for equipping a structure to be inspected, said installation consisting essentially of:
    at least one external circuit, which is external to said structure; and
    at least one device incorporated into said structure during the production of the structure, whereby said at least one incorporated device is able respectively (a) to receive electromagnetic signals from said at least one external circuit and transmit corresponding ultrasonic waves into the structure to be inspected, and (b) to receive ultrasonic waves from the structure and transmit corresponding electromagnetic signals to said at least one external circuit;
    wherein said at least one incorporated device has no electrical wire link with any said external circuit nor with any other said incorporated device of said installation, and wherein said at least one incorporated device consists of
    (a) a piezoelectric element for transmitting and receiving ultrasonic waves respectively in and from said structure and
    (b) a magnetic induction loop for receiving and transmitting electromagnetic signals respectively from and to said at least one external circuit, and
    wherein said piezoelectric element has electrodes connected to electrodes of said magnetic induction loop.

2. Installation according to claim 1, wherein said magnetic induction loop is constituted by a flat spiral of a flexible printed circuit, a positioning mark located on the surface of said structure being provided next to said spiral.

3. Installation according to claim 1, wherein said magnetic induction loop is constituted by a flat spiral of a flexible printed circuit etched directly onto the piezoelectric element.

4. Installation according to claim 1, wherein said external circuit is constituted in the form of a primary winding (of a transformer connected to an alternating current supply source and induction-coupled to said magnetic induction loop constituting the secondary of said transformer, said piezoelectric element in this case constituting a transmission source for ultrasonic waves in said structure.

5. Installation according to claim 1, wherein said external circuit is constituted in the form of a secondary winding of a transformer connected to a circuit for processing the signal and induction-coupled to said magnetic induction loop constituting the primary of said transformer, said piezoelectric element in this case constituting a receiver of ultrasonic waves transmitted in said structure.

6. Installation according to claim 1, wherein it comprises at least one first and one or more second piezoelectric elements incorporated into the structure, the first element being associated with a magnetic induction loop constituting the secondary of a first transformer induction-coupled to the primary winding constituted by an external circuit connected to an alternating current supply source, said first piezoelectric element in this case constituting a transmission source for ultrasonic waves in said structure, and the second element or elements, located at a distance from the first, each being associated with a magnetic induction loop constituting the primary of a second transformer induction-coupled to the secondary winding constituted by an external circuit connected to a circuit for processing the signal, said second piezoelectric element or elements in this case constituting one or more receivers of the ultrasonic waves transmitted in this structure to be inspected by the first piezoelectric element.

7. Installation according to claim 1, wherein it comprises, incorporated into said structure, one and the same piezoelectric element as an ultrasonic wave transmitter and as a receiver, for measuring the travel time of impulse waves transmitted by this element in the structure, from their reflection on a surface or an internal defect, and their return to the element.

8. Installation according to claim 4, wherein said windings are also produced in the form of flat spirals, attached to said structure next to said corresponding magnetic induction loops.

9. Installation according to claim 4, wherein a film of magnetic material is intercalated between each external transformer winding and the corresponding magnetic induction loop, incorporated into said structure.

10. Installation according to claim 1, wherein the structure, equipped with at least one piezoelectric element that is incorporated into it with its magnetic induction loop, is associated with a transmission source for electromagnetic signals in the frequency range required by a non-destructive inspection, and with an optical system for displaying the ultrasonic waves transmitted in the structure, said source and said system being located at a distance from said structure.

11. Installation according to claim 1, wherein said structure is a structure to be inspected.

12. Installation according to claim 1, wherein the magnetic induction loop is in the form of a flat spiral with several windings, of the printed circuit type.

13. Installation according to claim 12, wherein said piezoelectric element is disposed at the center of said spiral and is in the form of a thin wafer.

14. Installation according to claim 5, wherein said windings are also produced in the form of flat spirals, attached to said structure next to said corresponding magnetic induction loops.

15. Installation according to claim 5, wherein a film of magnetic material is intercalated between each external transformer winding and the corresponding magnetic induction loop, incorporated into said structure.

16. Installation according to claim 6, wherein said windings are also produced in the form of flat spirals, attached to said structure next to said corresponding magnetic induction loops.

17. Installation according to claim 6, wherein a film of magnetic material is intercalated between each external transformer winding and the corresponding magnetic induction loop, incorporated into said structure.

* * * * *